(12) United States Patent
Scott (10) Patent No.: US 8,758,434 B2
(45) Date of Patent: Jun. 24, 2014

(54) INTRAOCULAR LENS

(75) Inventor: James M. Scott, Millsap, TX (US)

(73) Assignee: Novartis AG, Basel (CH)

( * ) Notice: Subject to any disclaimer, the term of this patent is extended or adjusted under 35 U.S.C. 154(b) by 654 days.

(21) Appl. No.: 12/775,094

(22) Filed: May 6, 2010

(65) Prior Publication Data

US 2010/0217386 A1 Aug. 26, 2010

Related U.S. Application Data

(63) Continuation of application No. 11/619,045, filed on Jan. 2, 2007, now abandoned.

(51) Int. Cl.
*A61F 2/16* (2006.01)

(52) U.S. Cl.
USPC .......................... 623/6.4; 623/6.47; 623/6.43

(58) Field of Classification Search
USPC ...................... 623/6.37–6.45, 6.47
See application file for complete search history.

(56) References Cited

U.S. PATENT DOCUMENTS

| | | | |
|---|---|---|---|
| 4,122,556 A * | 10/1978 | Poler | 623/6.12 |
| 4,280,232 A | 7/1981 | Hummel | |
| 4,354,286 A | 10/1982 | Krasnov et al. | |
| 4,363,143 A | 12/1982 | Callahan | |
| 4,377,329 A | 3/1983 | Poler | |
| 4,434,515 A | 3/1984 | Poler | |
| 4,466,858 A | 8/1984 | Poler | |
| 4,477,931 A | 10/1984 | Kelman | |
| 4,494,256 A | 1/1985 | Radtke et al. | |
| 4,617,023 A | 10/1986 | Peyman | |
| 4,666,444 A * | 5/1987 | Pannu | 623/6.45 |
| 4,681,586 A | 7/1987 | Woods | |
| 4,711,638 A | 12/1987 | Lindstrom | |
| 4,753,655 A | 6/1988 | Hecht | |
| 4,804,361 A | 2/1989 | Anis | |
| 4,842,600 A | 6/1989 | Feaster | |
| 4,863,463 A * | 9/1989 | Tjan | 623/6.42 |
| 4,880,427 A | 11/1989 | Anis | |
| 4,950,290 A | 8/1990 | Kamerling | |
| 4,961,745 A | 10/1990 | Graham | |
| 4,963,149 A | 10/1990 | Anis | |
| 5,108,429 A * | 4/1992 | Wiley | 623/6.22 |
| 5,203,788 A * | 4/1993 | Wiley | 623/6.22 |
| 6,364,906 B1 | 4/2002 | Baikoff et al. | |
| 6,656,223 B2 | 12/2003 | Brady | |
| 6,932,839 B1 | 8/2005 | Kamerling et al. | |
| 6,960,231 B2 | 11/2005 | Tran | |
| 6,986,787 B1 | 1/2006 | Baker, Jr. | |
| 2003/0074060 A1 * | 4/2003 | Zadno-Azizi et al. | 623/6.33 |
| 2003/0114927 A1 * | 6/2003 | Nagamoto | 623/6.37 |
| 2003/0130732 A1 * | 7/2003 | Sarfarazi | 623/6.13 |
| 2003/0135272 A1 * | 7/2003 | Brady et al. | 623/6.37 |
| 2003/0149480 A1 * | 8/2003 | Shadduck | 623/6.41 |
| 2003/0204254 A1 * | 10/2003 | Peng et al. | 623/6.34 |
| 2004/0236423 A1 * | 11/2004 | Zhang et al. | 623/6.37 |
| 2006/0047339 A1 * | 3/2006 | Brown | 623/6.13 |

\* cited by examiner

*Primary Examiner* — Paul Prebilic
(74) *Attorney, Agent, or Firm* — Jonathan E. Prejean (57) ABSTRACT

An IOL having an optic and a peripheral stabilizing ring. The optic and the ring are connected by a flexible bridge. An area on the ring coinciding with a feature on the optic helps to locate the optic within the ring in an unstressed state until the capsular bag collapses and locks the optic into place.

8 Claims, 10 Drawing Sheets

INTRAOCULAR LENS

This application is a continuation of and claims priority to U.S. application Ser. No. 11/619,045 filed Jan. 2, 2007 now abandoned.

BACKGROUND OF THE INVENTION

This invention relates generally to the field of intraocular lenses (IOL) and, more particularly, micro-incision IOLs.

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

For many years, IOLs were made from a hard plastic, such as polymethylmethacrylate. As the optic of the IOL had a diameter of 5.5 mm to 6.5 mm, implanting the IOL required that the incision into the eye be enlarged to a size sufficient to allow the IOL to pass into the anterior chamber of the eye. Such a large incision can induce a distortion in the cornea, or induced astigmatism, post-operatively. More recently, IOL's have increasing been made from soft, foldable materials, such as silicone and soft acrylics. These foldable materials allow the IOL to be implanted through incisions that are generally less than 3 mm. Even the relatively small incision required for implantation of foldable IOLs can induce post-operative astigmatism, so there has been a desire to develop IOLs that can be implanted through even smaller incisions, on the order of 2 mm or less.

From a practical standpoint, there are limits on how small an IOL can be made. For example, the IOL generally must have an optic having a diameter of about 5.5 mm or greater for optimum optical performance. In addition, the IOL must be provided in a large range of optical powers, up to 30 diopters or more. These large powers limit how thin the optic can be made. Of course, increasing the refractive index of the material used to make the optic allows for a thinner optic. Current materials and designs permit the manufacture of very thin optics, having an extremely thin, almost knife-like, edge thickness. These extremely thin lenses, however, tend to be unstable to and distort when implanted within the capsular bag, requiring an encircling ring or equatorial band to be inserted into the capsular bag to help stabilize the capsular bag. The ring component of the IOL can be formed integrally with the optic or implanted as a separate component. If the ring is a separate component, the surgical procedure is increased in complexity because two is separate devices, the ring and the optic must be inserted into the eye, assembled and properly located within the capsular bag. Prior to the present invention, if the ring component is integrally formed with the optic, undesirable size and bulk is added, increased the require size of the incision.

Therefore, a need continues to exist for a safe and stable intraocular lens system that can be inserted through a very small incision and does not require assembly within the eye.

BRIEF SUMMARY OF THE INVENTION

The present invention improves upon the prior art by providing an IOL having an optic and a peripheral stabilizing ring. The optic and the ring are connected by a flexible bridge. An area on the ring coinciding with a feature on the optic helps to locate the optic within the ring in an unstressed state until the capsular bag collapses and locks the optic into place.

Accordingly, one objective of the present invention is to provide a safe and biocompatible intraocular lens.

Another objective of the present invention is to provide a safe and biocompatible intraocular lens that is easily implanted in the posterior chamber.

Still another objective of the present invention is to provide a safe and biocompatible intraocular lens that is stable in the posterior chamber.

Still another objective of the present invention is to provide a safe and biocompatible lens system that can be implanted through a small incision.

Still another objective of the present invention is to provide a safe and biocompatible lens system that helps reduce the incidence of PCO.

Still another objective of the present invention is to provide a safe and biocompatible lens system for use in cataract and/or clear lens exchange surgeries.

These and other advantages and objectives of the present invention will become apparent from the detailed description and claims that follow.

DETAILED DESCRIPTION OF THE PREFERRED EMBODIMENTS

Figure 1:
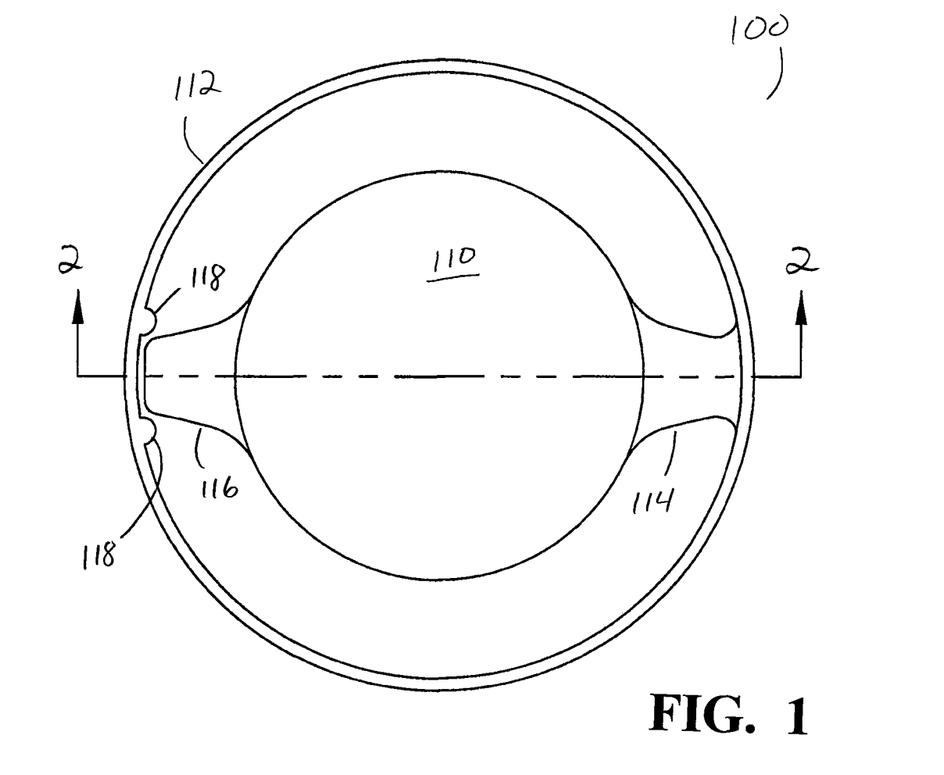
FIG. 1 is an enlarged perspective view of a first embodiment of the lens of the present system.
Figure 2:
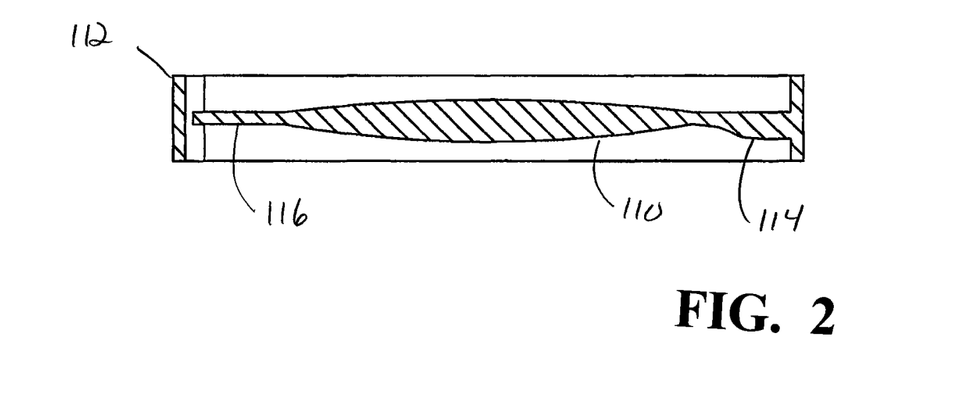
FIG. 2 is an enlarged cross-sectional view of a first embodiment of the lens of the present system taken at line 2-2 in FIG. 1.

As best seen in FIGS. 1 and 2, lens 100 of the present invention generally includes optic 110 and support ring 112 joined by bridge 114. As shown in the FIGs, optic 110 is integrally formed as a single contiguous piece with bridge 114 and support ring 112. Tab 116 is attached to optic 110 opposite bridge 114 so as to cooperate with corresponding locating feature 118 on support ring 112. Locating feature 118 is integrally molded with support ring 112 and in the embodiment illustrated in FIG. 1, consists of bumps or protuberances projecting inwardly from support ring 112 and toward optic 110. Support ring 112 is preferably formed in any suitable overall diameter, for example, between approximately 8.0 millimeters and 12.0 millimeters, a suitable interior diameter, for example, between approximately 6.0 millimeters and 8.5 millimeters and made from a soft, foldable material such as a soft acrylic, rubber elastomers, hydrogel or silicone. By way of example, support ring 112 may be made of rubber elastomers, such as butyl rubber, latex rubber, natural rubber, pure gum rubber, neoprene rubber, acrylonitrile rubber, styrene-butadiene rubber, ethylene-propylene diene monomer rubber, acrylonitrile-butadiene-styrene (ABS) rubber, epichlorohydrin rubber, hypalon rubber, silicone rubber and siloxane elastomers, such as poly(dimethylsiloxane), polyurethane rubber, viton rubber, ethylene-butylene rubber, isobutylene rubber and elastomers of polyphosphazenes, like poly(bis-trifluorethoxyphosphazene) oly(dimethylphosphazene) and poly(phenylmethylphosphazene). Preferably, support ring 112 may be formed so as to be opaque, such as by frosting or texturing the anterior and/or posterior surfaces of support ring 112, or support ring 112 may be relatively clear. Support ring 112 may also contain a chromophore to block ultraviolet and/or blue and/or green light, such chromophore(s) being well-known in the art.

Optic 110 is generally circular having a diameter for example, between approximately 4.0 millimeters and 7.0 millimeters. Optic 110 tapers from being relatively thick in the middle to having a relatively thin, or sharp, edge and is preferably integrally formed with and from the same material as support ring 112 and bridge 114. Optic 110 may also a chromophore to block ultraviolet and/or blue light, such chromophore(s) being well-known in the art, but unlike support ring 112, which may be opaque, optic 110 is optically clear. Tab 116 is also integrally formed with optic 110 opposite bridge 114.

Figure 17:
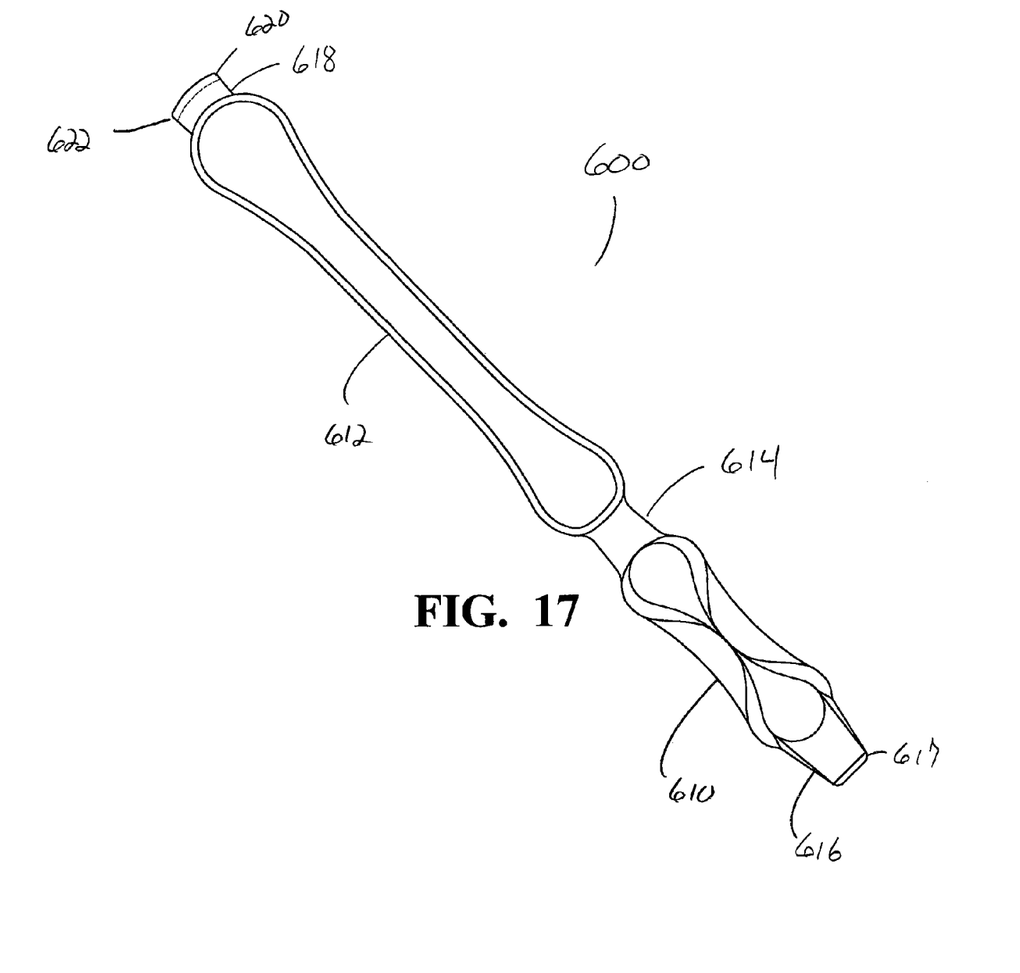
FIG. 17 is an enlarged prospective view of a sixth embodiment of the lens of the present invention illustrating the lens in a stretched and elongated form, suitable for implantation through a small incision.

When lens 100 is implanted in an eye, tab 116 and feature 118 help to center optic 110 in an unstressed state within ring 112 until lens 100 becomes naturally fixated within the eye. The construction of tab 116 and feature 118, allows the lens to be elongated and reduced in cross-section, as illustrated in FIG. 17, for implantation through a relative small (2.4 mm or less) incision.

Figure 3:
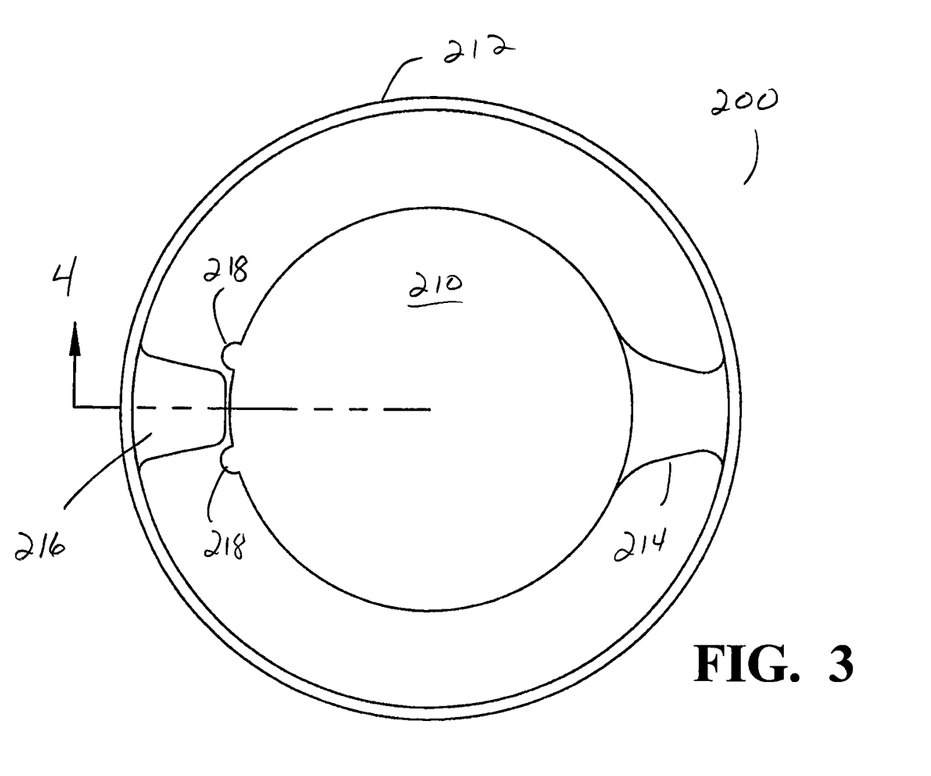
FIG. 3 is an enlarged perspective view of a second embodiment of the lens of the present system.
Figure 4:
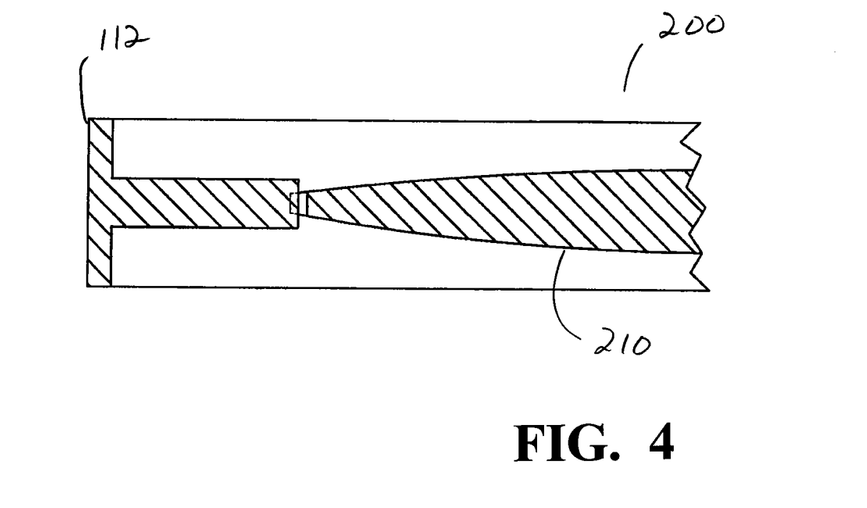
FIG. 4 is an enlarged partial cross-sectional view of a second embodiment of the lens of the present system taken at line 4 in FIG. 3.

As best seen in FIGS. 3 and 4, lens 200 of the present invention generally includes optic 210 and support ring 212 joined by bridge 214. As shown in the FIGs, optic 210 is integrally formed as a single contiguous piece with bridge 214 and support ring 212. Tab 216 is attached to support ring 212 opposite bridge 214 so as to cooperate with corresponding locating feature 218 on optic 210. Tab 216 is integrally molded with support ring 212. Support ring 212 is of construction and materials similar to support ring 112.

Optic 210 is of construction and materials similar to optic 110. Feature 218 is integrally formed with optic 210 opposite bridge 214 and in the embodiment illustrated in FIG. 3, consists of bumps or protuberances projecting outwardly from optic 210 and toward tab 216.

When lens 200 is implanted in an eye, tab 216 and feature 218 help to center optic 210 within ring 212 until lens 200 becomes naturally fixated within the eye. The construction of tab 216 and feature 218, allows the lens to be elongated and reduced in cross-section, as illustrated in FIG. 17, for implantation through a relative small (2.4 mm or less) incision.

Figure 5:
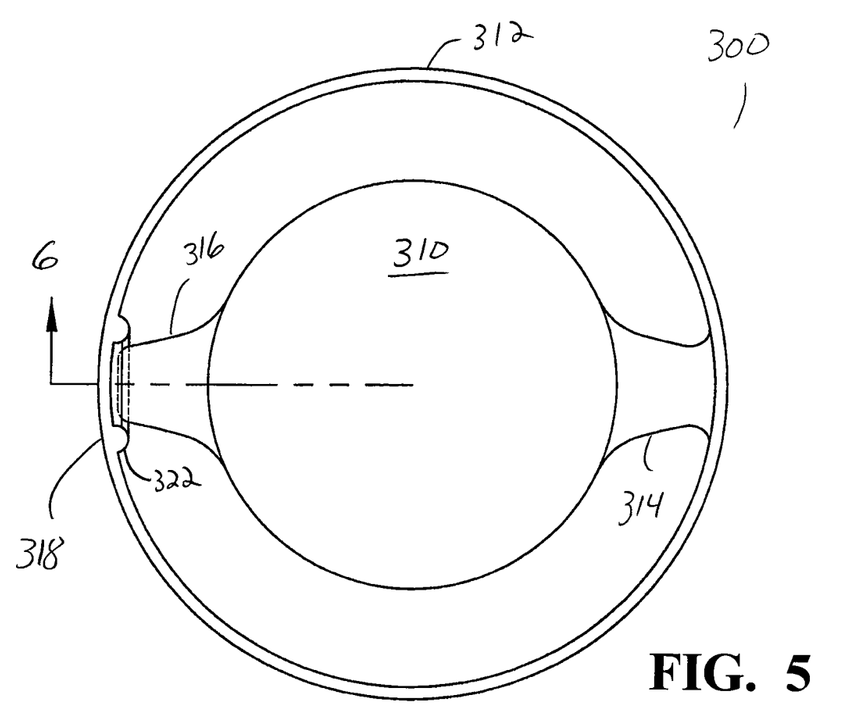
FIG. 5 is an enlarged perspective view of a third embodiment of the lens of the present system.
Figure 6:
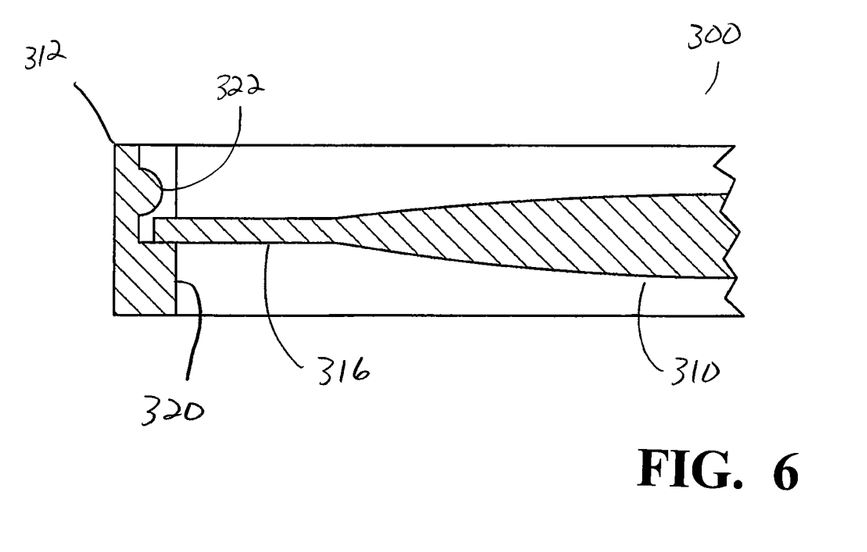
FIG. 6 is an enlarged partial cross-sectional view of a third embodiment of the lens of the present system taken at line 6 in FIG. 5.

As best seen in FIGS. 5 and 6, lens 300 of the present invention generally includes optic 310 and support ring 312 joined by bridge 314. As shown in the FIGs, optic 310 is integrally formed as a single contiguous piece with bridge 314 and support ring 312. Tab 316 is attached to optic 310 opposite bridge 314 so as to cooperate with corresponding locating feature 318 on support ring 312. Locating feature 318 is integrally molded with support ring 312 and in the embodiment illustrated in FIGS. 5 and 6, consists of ledge 320 and locking ridge 322 projecting inwardly from support ring 312 and toward optic 310.

Optic 310 is of construction and materials similar to optic 110. Tab 316 is also integrally formed with optic 310 opposite bridge 314.

When lens 300 is implanted in an eye, tab 316 and feature 318 help to center optic 310 within ring 312 until lens 300 becomes naturally fixated within the eye. The construction of tab 316 and feature 318, allows the lens to be elongated and reduced in cross-section, as illustrated in FIG. 17, for implantation through a relative small (2.4 mm or less) incision.

Figure 7:
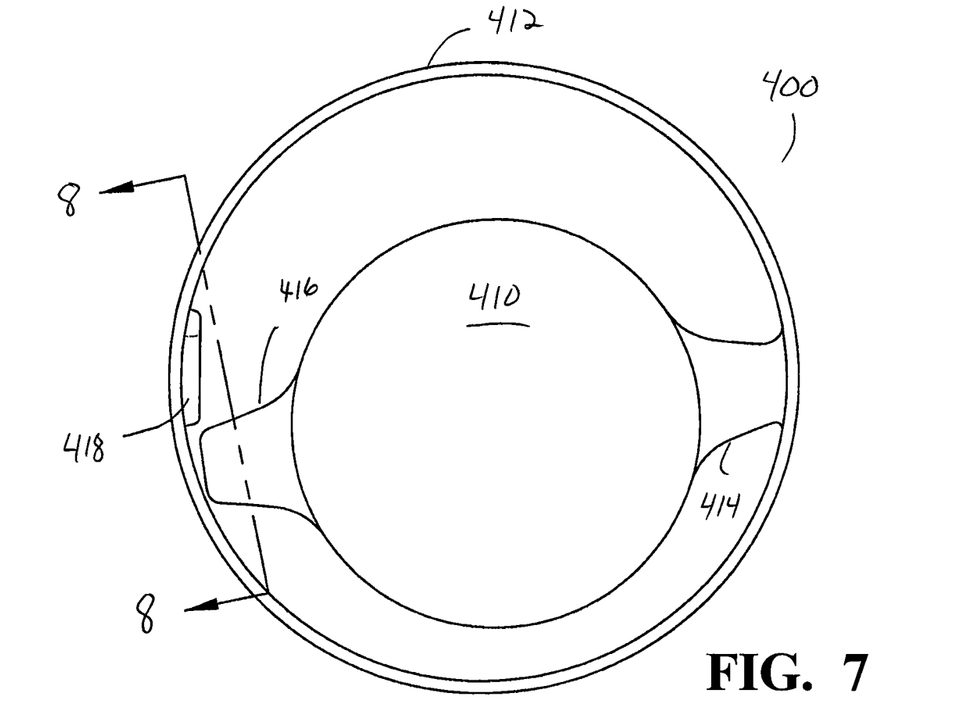
FIG. 7 is an enlarged perspective view of a fourth embodiment of the lens of the present system in an unlocked position.
Figure 8:
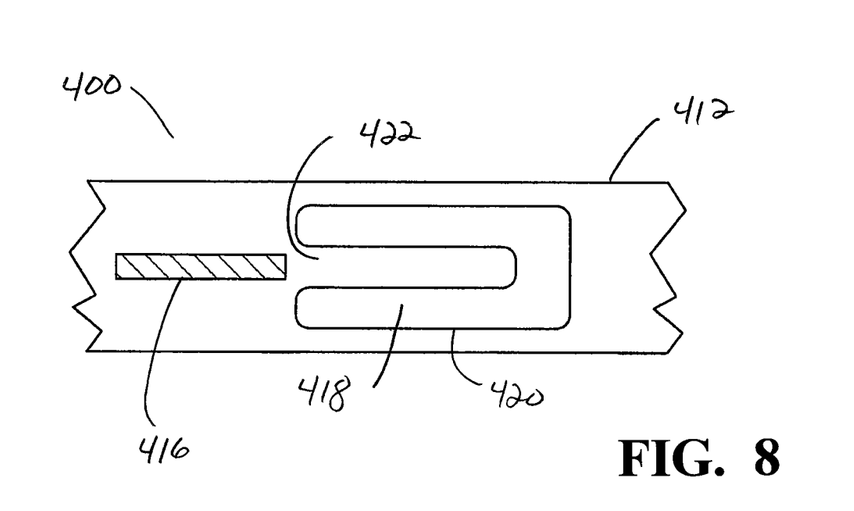
FIG. 8 is an enlarged partial cross-sectional view of a fourth embodiment of the lens of the present system taken at line 8-8 in FIG. 7.
Figure 9:
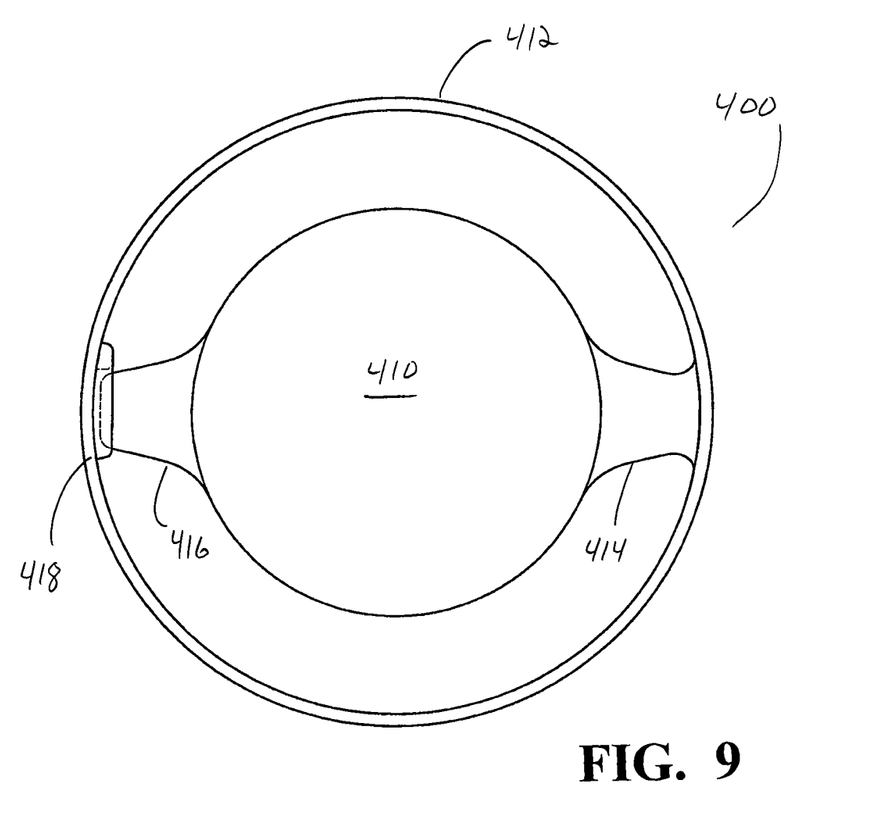
FIG. 9 is an enlarged perspective view of a fourth embodiment of the lens of the present system similar to FIG. 7, but illustrating the lens in a locked position.

As best seen in FIGS. 7, 8 and 9, lens 400 of the present invention generally includes optic 410 and support ring 412. Optic 410 is connected to support ring 412 by bridge 414. Tab 416 is attached to optic 410 opposite bridge 414 so as to cooperate with corresponding locating feature 418 on support ring 412. Locating feature 418 is integrally molded with support ring 412 and in the embodiment illustrated in FIGS. 7, 8 and 9, consists of ledge 420 having slot 422 projecting inwardly from support ring 412 and toward optic 410.

Optic 410 is of construction and materials similar to optic 110. Tab 416 is also integrally formed with optic 410 opposite bridge 414.

When lens 400 is implanted in an eye, tab 416 and feature 418 help to center optic 410 within ring 412 until lens 400 becomes naturally fixated within the eye. The construction of tab 416 and feature 418, allows the lens to be elongated and reduced in cross-section, as illustrated in FIG. 17, for implantation through a relative small (2.4 mm or less) incision. To insert tab 416 into slot 422 of feature 418, optic 410 may be manipulated so that bridge 414 is deformed, as shown in FIG.

7. Tab 416 can them be inserted into slot 422 and lens 400 returned to its normal shape, as illustrated in FIG. 9.

As best seen in FIGS. 10, 11, 12 and 13, lens 500 of the present invention generally includes optic 510 and support ring 512. Optic 510 is connected to support ring 512 by bridge 514. Tab 516 is attached to optic 510 opposite bridge 514 so as to cooperate with corresponding locating feature 518 on support ring 512. Locating feature 518 is integrally molded with support ring 512 and in the embodiment illustrated in FIGS. 10, 11 and 12, consists of ledge 520 having slot 522 projecting inwardly from support ring 512 and toward optic 510.

Optic 510 is of construction and materials similar to optic 110. Tab 516 is also integrally formed with optic 510 opposite bridge 514. Tab 516 contains locking rim 517 or 517' that cooperates with slot 522 in feature 518 to assist in locking tab 516 within feature 518.

Figure 10:
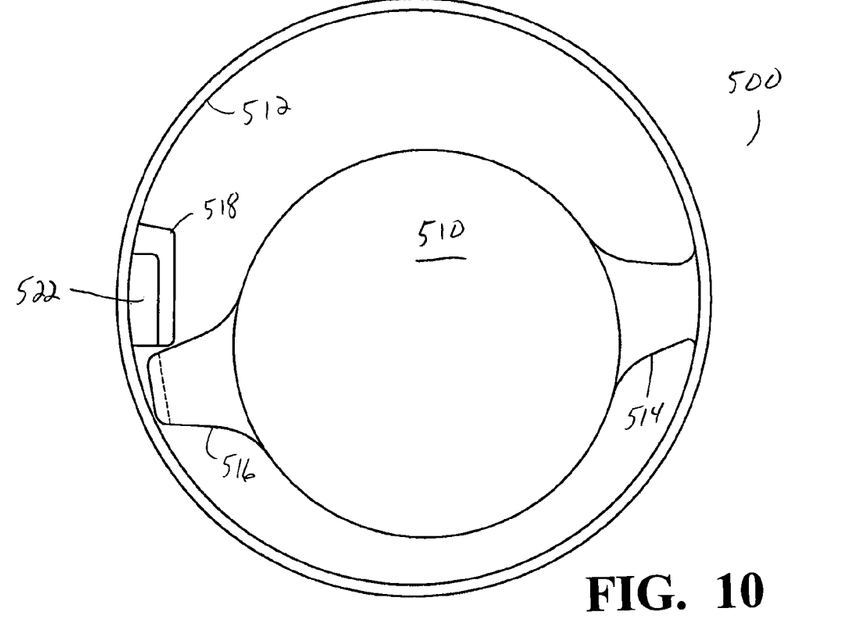
FIG. 10 is an enlarged perspective view of a fifth embodiment of the lens of the present system in an unlocked position.
Figure 11:
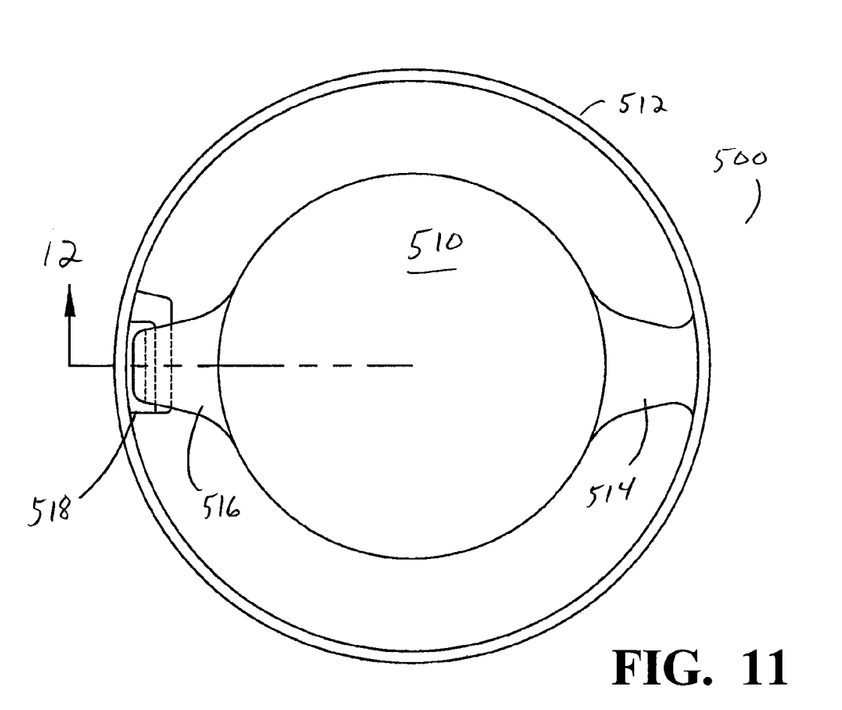
FIG. 11 is an enlarged perspective view of a fifth embodiment of the lens of the present system similar to FIG. 10, but illustrating the lens in a locked position.
Figure 12:
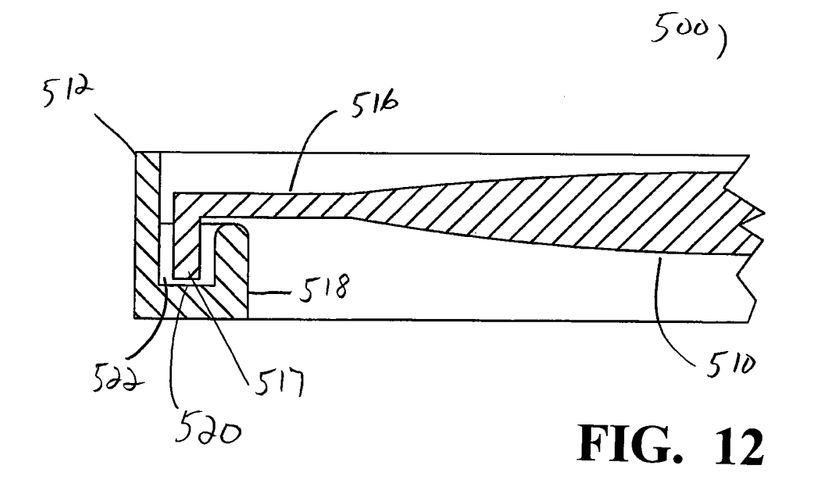
FIG. 12 is an enlarged partial cross-sectional view of a fifth embodiment of the lens of the present system taken at line 12 in FIG. 11.
Figure 13:
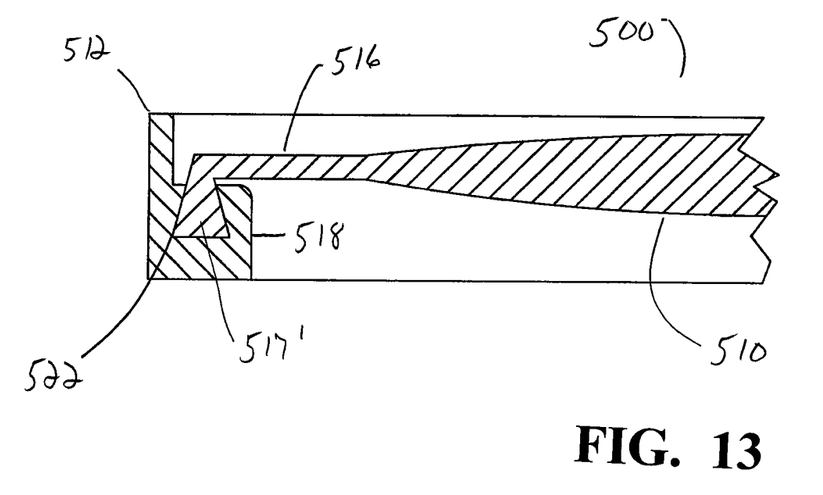
FIG. 13 is an enlarged partial cross-sectional view of a fifth embodiment of the lens of the present system similar to FIG. 12, but illustrating an alternative locking mechanism.

When lens 500 is implanted in an eye, tab 516 and feature 518 help to center optic 510 within ring 512 until lens 500 becomes naturally fixated within the eye. The construction of tab 516 and feature 518, allows the lens to be elongated and reduced in cross-section, as illustrated in FIG. 17, for implantation through a relative small (2.4 mm or less) incision. Following implantation, tab 516 is inserted into slot 522 in the manner described above. As best seen in FIG. 12, locking rim 517 fits within slot 522 of feature 518 so as to assist in holding tab 516 within feature 518. Alternatively, as seen in FIG. 13, locking rim 517 can be flared so as to dovetail into slot 522 and provide a more positive locking of tab 516 within feature 518. To insert tab rim 517 into slot 522 of feature 518, optic 510 may be manipulated so that bridge 514 is deformed, as shown in FIG. 10. Tab 516 can them be inserted into slot 522 and lens 500 returned to its normal shape, as illustrated in FIG. 11.

As best seen in FIGS. 14, 15, 16 and 17, lens 600 of the present invention generally includes optic 610 and support ring 612. Optic 610 is connected to support ring 612 by bridge 614. Tab 616 is attached to optic 610 opposite bridge 614 so as to cooperate with corresponding locating feature 618 on support ring 612. Locating feature 618 is integrally molded with support ring 612 and in the embodiment illustrated in FIGS. 14, 15, 16 and 17, consists of channel 620 having open slot 622 projecting inwardly from support ring 612 and toward optic 610.

Optic 610 is of construction and materials similar to optic 110. Tab 616 is also integrally formed with optic 610 opposite bridge 614. Tab 616 contains "T"-shaped locking rim 617 that cooperates with slot 622 in feature 618 to assist in locking tab 616 within feature 618.

Figure 14:
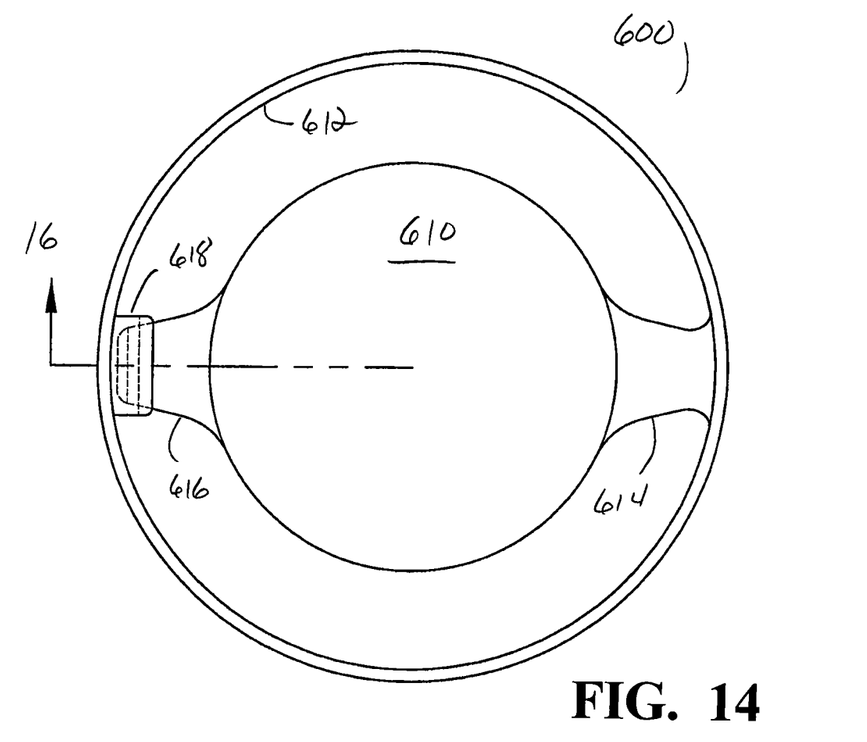
FIG. 14 is an enlarged perspective view of a sixth embodiment of the lens of the present system illustrating the lens in a locked position.
Figure 15:
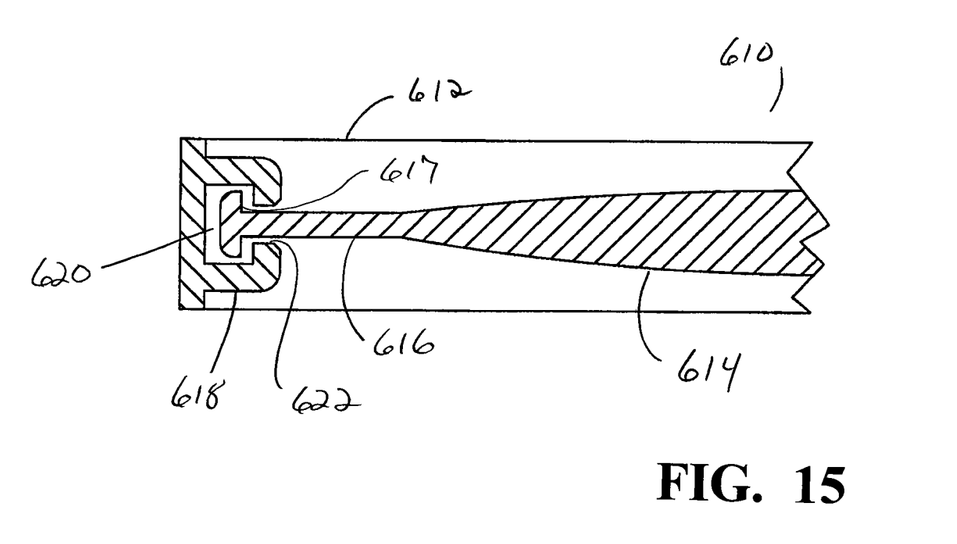
FIG. 15 is an enlarged partial cross-sectional view of a sixth embodiment of the lens of the present system taken at line 15 in FIG. 14.
Figure 16:
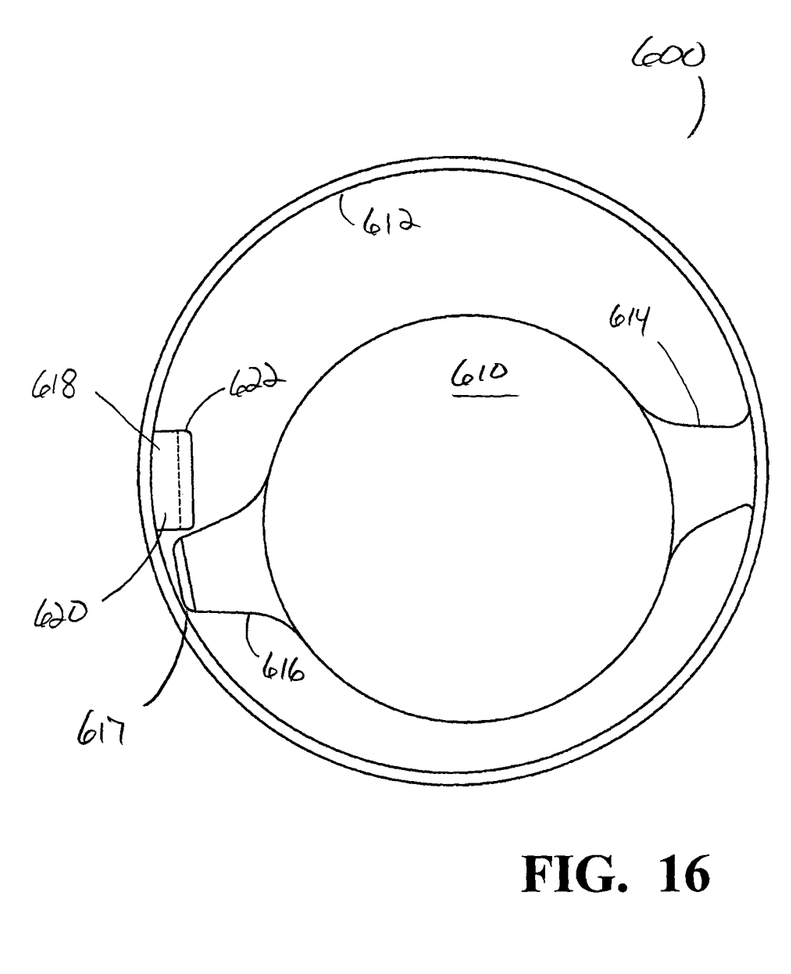
FIG. 16 is an enlarged perspective view of a sixth embodiment of the lens of the present system, similar to FIG. 14, but illustrating the lens in an lo unlocked position.

When lens 600 is implanted in an eye, tab 616 and feature 618 help to center optic 610 within ring 612 until lens 600 becomes naturally fixated within the eye. The construction of tab 616 and feature 618, allows the lens to be elongated and reduced in cross-section, as illustrated in FIG. 17, for implantation through a relative small (2.4 mm or less) incision. Following implantation, tab 616 is inserted into slot 622 in the manner described above. As best seen in FIG. 15, locking rim 567 fits within slot 622 of feature 618 so as to assist in holding tab 616 within feature 618. To insert tab rim 617 into slot 622 of feature 618, optic 610 may be manipulated so that bridge 614 is deformed, as shown in FIG. 16. Rim 617 can them be inserted into slot 622 and lens 600 returned to its normal shape, as illustrated in FIG. 14.

This description is given for purposes of illustration and explanation. It will be apparent to those skilled in the relevant art that changes and modifications may be made to the invention described above without departing from its scope or spirit.

The invention claimed is:

1. An intraocular lens, comprising:
   a) a support ring configured in a circular shape, the support ring having an inner surface having an inner diameter between 6.0 millimeters and 8.5 millimeters in the circular shape;
   b) an optic integrally formed-with the support ring, comprising a bridge on one side of the optic, wherein the bridge, the optic and the support ring are formed as a single contiguous piece from a soft, foldable material;
   c) a tab integrally formed with the optic on another side of the optic, the tab comprising a free end opposite the optic, the free end of the tab extending to the inner surface of the support ring in the circular shape; and
   d) a locating feature on the inner surface of the support ring, the locating feature sized to allow the free end of the tab to be inserted therein, the locating feature cooperating with the tab when the free end is inserted into the locating feature so as to center the optic within the support ring in an unstressed state.

2. The lens of claim 1 wherein the locating feature comprises a channel with a slot.

3. The lens of claim 1 wherein the locating feature comprises bumps or protuberances projecting inwardly from the support ring and toward the optic.

4. The lens of claim 1 wherein the locating feature comprises a ledge and a locking ridge.

5. The lens of claim 1 wherein the locating feature comprises a ledge having a slot, the locating feature projecting inwardly from the support ring and toward the optic.

6. The lens of claim 1 wherein the locating feature comprises a channel having an open slot, the channel projecting inwardly from the support ring and toward the optic.

7. An intraocular lens, comprising:
   a) a support ring configured in a circular shape, the support ring having an inner surface having an inner diameter between 6.0 millimeters and 8.5 millimeters in the circular shape;
   b) an optic integrally formed-with the support ring, comprising a bridge on one side of the optic, wherein the bridge, the optic and the support ring are formed as a single contiguous piece from a soft, foldable material;
   c) a tab integrally formed with the support ring extending from the inner diameter of the circular shape to the optic, the tab comprising a free end opposite the support ring; and
   d) a locating feature on the optic, the locating feature sized to allow the free end of the tab to be inserted therein, the locating feature cooperating with the tab when the free end is inserted into the locating feature so as to center the optic within the support ring in an unstressed state.

8. The lens of claim 7 wherein the locating feature comprises bumps or protuberances projecting outwardly from the optic and toward the support ring.

* * * * *